US010624312B2

(12) United States Patent
Breitenstein

(10) Patent No.: US 10,624,312 B2
(45) Date of Patent: Apr. 21, 2020

(54) DEVICE FOR MEASURING THE GASTRIC PRESSURE AND THE GASTRIC MOTILITY OF A LIVESTOCK ANIMAL

(71) Applicant: DROPNOSTIX GMBH, Potsdam (DE)

(72) Inventor: Michael Breitenstein, Potsdam (DE)

(73) Assignee: DROPNOSTIX GMBH, Potsdam (DE)

( * ) Notice: Subject to any disclaimer, the term of this patent is extended or adjusted under 35 U.S.C. 154(b) by 0 days.

(21) Appl. No.: 16/062,119

(22) PCT Filed: Dec. 16, 2016

(86) PCT No.: PCT/EP2016/081622
§ 371 (c)(1),
(2) Date: Jun. 14, 2018

(87) PCT Pub. No.: WO2017/103239
PCT Pub. Date: Jun. 22, 2017

(65) Prior Publication Data
US 2018/0368362 A1    Dec. 27, 2018

(30) Foreign Application Priority Data

Dec. 18, 2015   (DE) .................. 10 2015 122 293

(51) Int. Cl.
*A01K 11/00*    (2006.01)
*A61B 5/00*    (2006.01)
(Continued)

(52) U.S. Cl.
CPC .............. *A01K 11/007* (2013.01); *A61B 5/01* (2013.01); *A61B 5/036* (2013.01); *A61B 5/073* (2013.01);
(Continued)

(58) Field of Classification Search
CPC ................ A01K 11/007; A01K 29/005; A61B 2503/40; A61B 5/01; A61B 5/036;
(Continued)

(56) References Cited

U.S. PATENT DOCUMENTS 6,099,482 A     8/2000  Brune et al.
2005/0061079 A1*  3/2005  Schulman ............ A61B 5/0031
                                                 73/715
(Continued)

FOREIGN PATENT DOCUMENTS

DE          29911803         9/1999
DE          60017916         3/2006
(Continued)

OTHER PUBLICATIONS

Lawrence Yu et al: "Chronically Implanted Pressure Sensors: Challenges and State of the Field", Sensors, vol. 14, No. 11, Oct. 31, 2014, pp. 20620-20644.

*Primary Examiner* — Nader Bolourchi
(74) *Attorney, Agent, or Firm* — JMB Davis Ben-David

(57) ABSTRACT

The invention relates to a device for permanently detecting the gastric pressure, the gastric temperature, the gastric motility and the movement of a livestock animal, in particular a ruminant, comprising a, for example, bolus-shaped body (14), said body (14) comprising the following components: a pressure sensor (9), a telemetric device (9) for transmitting measuring values, and a gas-tight interior space (12), wherein a wall of the gas-tight interior space (12) comprises in some regions an elastic material which is deformable by the gastric pressure of a livestock animal, and wherein the pressure sensor (9) is designed to detect the pressure in the gas-tight interior space (12). According to the invention, said device is designed such that it permanently remains in the stomach of the livestock animal when it is applied to the livestock animal.

17 Claims, 3 Drawing Sheets

(51) Int. Cl.
*A61B 5/01* (2006.01)
*A61B 5/03* (2006.01)
*A61B 5/07* (2006.01)
*A61B 5/11* (2006.01)
*A01K 29/00* (2006.01)

(52) U.S. Cl.
CPC .......... *A61B 5/1107* (2013.01); *A61B 5/4238* (2013.01); *A61B 5/6871* (2013.01); *A01K 29/005* (2013.01); *A61B 2503/40* (2013.01)

(58) Field of Classification Search
CPC ..... A61B 5/073; A61B 5/1107; A61B 5/4238; A61B 5/687
See application file for complete search history.

(56) References Cited

U.S. PATENT DOCUMENTS

| | | | | |
|---|---|---|---|---|
| 2005/0065571 | A1* | 3/2005 | Imran | A61N 1/36007 607/41 |
| 2005/0175665 | A1* | 8/2005 | Hunter | A61K 45/06 424/423 |
| 2007/0129703 | A1 | 6/2007 | Andrea et al. | |
| 2007/0156015 | A1 | 7/2007 | Gilad | |
| 2008/0236500 | A1 | 10/2008 | Hodges et al. | |
| 2010/0130837 | A1 | 5/2010 | Matott | |
| 2012/0116182 | A1* | 5/2012 | Wong | A61F 5/0026 600/301 |
| 2012/0277550 | A1* | 11/2012 | Rosenkranz | A01K 11/007 600/302 |
| 2012/0310054 | A1 | 12/2012 | Birk | |
| 2016/0353710 | A1* | 12/2016 | Laporte Uribe | G01N 21/3577 |

FOREIGN PATENT DOCUMENTS

| | | |
|---|---|---|
| DE | 102014101875 | 8/2015 |
| EP | 1969998 | 9/2008 |
| GB | 2455700 | 6/2009 |
| WO | WO 01/13712 A1 * | 3/2001 |
| WO | 2011/079338 | 7/2011 |
| WO | 2012/047150 | 4/2012 |

* cited by examiner

DEVICE FOR MEASURING THE GASTRIC PRESSURE AND THE GASTRIC MOTILITY OF A LIVESTOCK ANIMAL

CROSS-REFERENCE TO RELATED APPLICATIONS

This is the U.S. National Stage of International Application No. PCT/EP2016/081622 filed Dec. 16, 2016, which was published in English under PCT Article 21(2), and which in turn claims the benefit of German Patent Application No. 10 2015 122 293.0 filed Dec. 18, 2015.

DESCRIPTION

The invention relates to a device for permanently, in particular exclusively, detecting the gastric pressure, gastric temperature, gastric motility and movement of a ruminant according to Claim 1, and to a two-part device for detecting the gastric motility of a ruminant according to Claim 15. A method for measuring gastric pressure in livestock is also disclosed according to Claim 16.

In the absence of technical aids, the production diseases associated with modern agriculture, such as for example subacute ruminal acidosis (SARA), are for the most part only possible to detect subsequently or indirectly.

SARA in particular is a serious agricultural problem in both health and economic terms. SARA may for instance be a trigger for reduced food intake, reduced milk yield, diarrhoeal diseases, inflammation of the ruminal mucosa, hoof diseases (laminitis, bleeding from the sole and sole ulcers) and lameness. Financial losses amount to EUR 400 per cow during lactation.

Hitherto known technical solutions for diagnosing SARA involve determining ruminal pH. Two basic methods are available for this purpose:
a) sampling the ruminal juice, or
b) continuous measurement by means of a sensor accommodated in the rumen.

With regard to a), sampling proceeds by rumen puncture (rumenocentesis) under local anaesthesia or via a stomach or gastric tube introduced orally. Due to the method used, the values determined in this manner include saliva, for which reason the values are on average 0.5 pH units (0.2 to 1.9 pH units) higher than measurements obtained with comparative measurements by rumenocentesis or fistula. The drawback associated with this procedure is that it involves single point measurements which can only be carried out by skilled specialist personnel. A further complicating factor with rumenocentesis is that the surgical intervention can have side-effects and there is a risk of infection for the animal. Furthermore, contamination with blood can influence the result in this latter method.

With regard to b), as explained in [DE 600 17 916 T2] [WO 2011/079338 A2] [GB 2 455 700 A], a sensor system is here introduced orally into the rumen in bolus form in order to continuously transmit the pH of the ruminal juice by telemetry. The difficulty here is that the probe is microbiologically colonised over the course of time and increasingly forms its own microenvironment which is measured instead of the ruminal juice which should be measured. In laboratory diagnostics, a ruminal juice pH of below 6.0 means acute ruminal acidosis. If the pH is below 5.6 for more than 3 hours per day, SARA can be assumed. The fact that animals which do not appear unhealthy also exhibit pH values which, by definition, would suggest ruminal acidosis, introduces a degree of uncertainty into existing diagnostic practices.

A further possibility for detecting SARA involves measuring ruminal activity and may be considered an indirect method. SARA is known to be accompanied by reduced ruminal movement. It has not been conclusively clarified whether the reduced ruminal movement is the result of the change in pH or whether the latter changes as a result of the ruminal movement.

In general, the challenge is to isolate clearly and sufficiently accurately the actual ruminal movement against the background of the movement of the animal in question. [DE 299 11 803 U1] describes a device for determining gastric motility which detects the movement of the stomach with a piezoelectric sensor element. This, however, has the disadvantage that merely bending the sensor element generates evaluable signals. In addition, pressure changes in the organ are not detected if they do not bring about any deformation of the sensor element.

Alternatively, an acceleration sensor located in the organ under investigation can measure organ movement, but such an acceleration sensor also detects the movements of the animal, such that no unambiguous conclusions about organ movement can be drawn.

A further advantage of such intestinal movement measurements is that long-term measurements are possible which are not influenced by biofilm or microbiological growth, as is known from pH measurement methods.

It should furthermore be noted that even within the same animal population there may be major fluctuations in status parameters and only by observing the distinctive features of an individual over time can a clear diagnosis be obtained.

Another economically relevant parameter is identification of the period of *oestrus*. The intercalving interval, an economic indicator for dairy farms, can only be kept as short as possible if the optimum insemination time is known. If the optimum insemination time is missed, the intercalving interval is extended. Today's high-yield dairy cows exhibit *oestrus* less markedly and for a shorter period. In addition to the tolerance reflex, which is a reliable indicator of *oestrus*, during the period of *oestrus* the movement activity of cattle in *oestrus* is around four times higher than that of those which are not in *oestrus*.

The object of the invention is therefore that of providing a device with which gastric pressure and gastric motility on the one hand, and the movements of a livestock animal on the other hand, can be reliably determined over a period of a number of days.

The problem of the invention is solved by a device of the initially stated type according to Claim 1 and Claim 15. Advantageous configurations of the invention are stated in the subclaims and are described below.

The invention provides that such a device for permanently, in particular exclusively, detecting the gastric pressure, gastric temperature, gastric motility and movement of a livestock animal, in particular of a ruminant, has a body which is preferably configured in bolus form, i.e. the body is of elongate configuration (in an axial direction) and, in the axial direction, has two free mutually opposing ends (one such end, on which a pressure sensor may be provided, is herein also denoted the upper end), said ends being rounded (to reduce any risk of injury) and the body having the following components:
  a telemetric device for transmitting measured values,
  a gas-tight interior, one wall of the gas-tight interior having in places a resilient material or a resilient region, which material or region is deformable by the gastric pressure, and the pressure sensor being configured to detect the pressure in the gas-tight interior, and wherein the device and in particular the body is constructed such that it remains permanently in the stomach of the livestock animal when it has been administered to the livestock animal and in particular is not excreted by rumination or digestion.

In this context, permanent means in particular that the device can only be removed from the stomach of the livestock animal after death or by surgery.

Ruminants have a plurality of stomachs which digest their diet. In a ruminant, the stomach in this connection in particular, but not necessarily exclusively, denotes the ruminant's rumen.

The device is advantageously usable in ruminants, in particular in cattle, in particular in dairy cows.

The device may be introduced into the livestock animal's stomach for example via its gullet. In the stomach, it can detect gastric pressure and the movements of the stomach, i.e. gastric motility, in order to obtain measured values for the intended period of operation, a minimum of 60 days being of relevance. A longer period of operation can be achieved by a correspondingly adapted energy supply.

By replacing chemical measurement methods with purely physical measurements (ruminal or gastric movement) which are in particular distinguished in that they are particularly economical on power, it is possible to achieve periods of operation of a number of months and even years using this device.

An essential component of the device is the gas-tight interior comprising the resilient material or the resilient region which can deform as a result of the externally acting forces. The pressure sensor is configured to detect the resultant pressure change in the gas-tight interior by means of suitable, for example piezoelectric, resistive, capacitive, optical or magnetic, sensors, wherein this may if necessary proceed using a measurement transducer.

The movement of the stomach in which the device is located or the actual medium surrounding it exerts a force on the device, specifically on the resilient material, which deforms it in the event of appropriate gastric activity. As a consequence, a pressure change occurs in the gas-tight interior which is detected by the pressure sensor.

The measurement data from the pressure sensor may then be evaluated, for example by means of an electrical circuit, and forwarded to a microcontroller in which further processing steps take place. The telemetric device is configured to send the measurement data or also any processed measurement data to a receiver which is set up outside the livestock animal. Typical frequency bands and transmission strengths which are non-hazardous to the livestock animal are used for this purpose.

The gas-tight interior contains a medium, for example a gas, a gas mixture, a fluid, a solution or a gel.

In a preferred variant, the resilient material or the resilient region includes an elastomer (for example latex or silicone) in the form of a bubble or consists of the elastomer in bubble form. The stability of the body in mechanical terms and in terms of its specific environment can be achieved by the body including for example POM (polyoxymethylene), PVC (polyvinyl chloride) or PEEK (polyetherether ketone) or being sheathed with these or other biocompatible polymers.

The body, or optionally bolus for short, can be encapsulated with a polymer (for example epoxy resin) and is preferably watertight.

The body is for example in the form of a pill.

A device having these features can detect any application of force in the stomach of a ruminant, whether by deformation (for example bending or flexing) or statically acting forces (for example slowly rising or declining pressure). The advantage of measuring the movement or activity of the organ in which the device is located is that the movement of the organ under investigation is largely independent of the basic movement of the animal.

In a preferred embodiment of the invention, the body has an average density of greater than 2.3 g/cm$^3$ and in particular less than 3.0 g/cm$^3$, wherein the density is particularly preferably 2.8 g/cm$^3$.

These average densities are sufficiently high to ensure that the device remains permanently in the stomach of the livestock animal.

In one embodiment of the invention, the body has a volume of between 50 cm$^3$ and 250 cm$^3$, preferably between 70 cm$^3$ and 160 cm$^3$, wherein the volume particularly preferably amounts to 150 cm$^3$. These size ranges advantageously ensure the compatibility of the device in the stomach of the livestock animal, in particular of the cow, and simultaneously provide enough space for installing a sufficiently large energy source for the electronics, in particular for the telemetric device, in the body (for example bolus).

The energy supply and energy management of the device according to the invention are in particular designed such that active operation of the device, i.e. for example intermittent or periodic measurements by the sensors of the device and telemetric transmission of the measurement data to a receiver, is possible for a period of at least one year.

In a preferred variant of the invention, the wall of the gas-tight interior is formed at least in places by a resilient hollow body projecting (or protruding) out from the body, wherein the hollow body is deformable by forces acting thereon in the stomach of the livestock animal, wherein the pressure sensor is configured to detect a deformation of the hollow body on the basis of a pressure change in the gas-tight interior. Such a deformation can for example be brought about by movements of the stomach or by a static pressure change in the stomach. The hollow body can be firmly connected to the pressure sensor for this purpose.

The combination of the hollow body as a probe with a pressure sensor thus guarantees that the activity or movement of the organ in question can be reliably recorded.

The protruding hollow body advantageously ensures that, in addition to the gastric pressure of the livestock animal, it is also possible to detect the gastric motility of the livestock animal.

In a preferred embodiment of the invention, the hollow body can be flexed by forces which arise from movements of the stomach of a livestock animal, wherein the hollow body is provided and configured to be flexed by said forces.

Flexure of the hollow body accordingly results in a pressure jump in the gas-tight interior which is detectable by the pressure sensor. Such a jump in pressure is clearly recordable in the measurement signals and can be specifically evaluated using suitable algorithms.

A further embodiment of the invention provides that the hollow body is of tubular, in particular cylindrical, configuration.

This shape of the hollow body is particularly suitable for ensuring a hollow body which can be flexed. The longer is the tubular hollow body, the more easily it can be flexed, such that the device can be adapted to the particular species of livestock animal by different lengths of the hollow body.

In a further embodiment, the resilient region or resilient material is configured as a membrane (for example circular membrane) which is located above the interior and bounds or seals the latter relative to the outside.

In a further embodiment of the invention, the body has a means which is configured to connect the hollow body or the membrane detachably to the body, such that the hollow body is replaceable if, for example, the device is to be used in a further animal. A hollow body/membrane which may have suffered severe wear can accordingly be exchanged comparatively simply without having to replace the complete body.

Such means may for example be embodied by a screw or clip connection. A corresponding closure means is preferably of annular construction.

In a preferred embodiment of the invention, the device has a temperature sensor which is designed to detect a gastric temperature in the livestock animal when the device is in the stomach of the livestock animal, and/or wherein the device comprises a motion sensor, which in particular has an acceleration sensor, wherein the motion sensor is designed to detect the movement activity of the livestock animal.

Such a motion sensor which determines the overall movement of the animal makes it possible, by logging the determined movement activity of the livestock animal, to draw conclusions as to the *oestrus* of the livestock animal, since, as explained above, *oestrus* is accompanied by modified movement activity of the livestock animal.

The advantage of such an integrated motion sensor is that the movement of the livestock animal can be detected independently of any grazing movements of the livestock animal (for example lowering the head during grazing), which is not guaranteed in the case of a collar sensor.

A temperature sensor makes it possible to identify diseases or even calving time.

This temperature sensor may allow conclusions to be drawn regarding drinking behaviour. Since the water which has been drunk is for the most part colder than the rumen or medium in the rumen, water intake results in a drop in temperature in the rumen. When plotted on a graph against time, the temperature measurements during intake of relatively cold water thus take the form of downwardly directed peaks. If the volume of the rumen is known, the quantity of liquid taken in can be estimated or approximated on the basis of an evaluation of the hysteresis or temperature profile during water intake.

In particular, correlated evaluation of movement and temperature data significantly increases the *oestrus* identification rate, such that a comparatively distinctly more reliable statement can be made regarding the state of *oestrus* of the livestock animal, since *oestrus* is associated with a characteristic temperature curve.

While for example *oestrus* or disease can indeed be identified by the isolated detection of parameters, such as for example body temperature alone, such detection has only limited suitability for making accurate statements regarding the precise state of the animal. The combination of a plurality of vital parameters measured in association in livestock animals, such as for example measurements of body temperature, physical movement or animal activity and ruminal motility, in particular derived from an anisotropic pressure measurement in the digestive apparatus of the livestock animal, allows a more differentiated assessment of the state of the animal. In particular, by correlating or linking the parameters body temperature, movement activity and ruminal motility, these interrelated parameters can be used to draw very accurate conclusions for example regarding animal health status on the basis of clear patterns. For instance, a body temperature which declines gradually over three days with a subsequent rise by 1 K, in combination with ruminal motility which declines gradually over three days and animal activity which gradually increases over three days is a clear indication of *oestrus* in a cow. Measuring just one of the above-stated parameters alone is incapable of achieving the significance of the three correlated parameters.

In a further embodiment of the invention, the telemetric device is designed to process the measurement data of the pressure sensor and in particular the measurement data of the temperature sensor and/or the motion sensor and to send the processed data to a receiver.

In a preferred embodiment, the sensor or sensors are in direct contact with the telemetric device of the body, which device, preferably with the assistance of a microcontroller, transmits the results to a base station either automatically or when requested or queried. In a preferred embodiment, the acquired data can be evaluated or displayed with the assistance of a computer. It is likewise possible to process the data as early as on the microcontroller in the device, the microcontroller in particular converting, saving or time-stamping these data and/or transmitting them to the telemetric device.

The device contains an unambiguous identifier, which is either fixedly predetermined or can be freely assigned by the user, wherein a combination of the two variants may also be used. According to the invention, the device can automatically or when queried display the status of the device and/or an alarm at the base station.

The data determined by the pressure sensor and, if present, also the data from the motion sensor and temperature sensor are preferably saved in a memory integrated in the device and, either at defined intervals or when queried, transmitted to the base station with the assistance of the telemetric device. On the base station, the data are in particular collected and displayed by the data acquisition device used by the user. The user can retrieve the data compiled on the base station and display the time profile of the measurement data for an animal or, according to the invention, make a comparison with a group of animals in order to draw conclusions regarding their health status.

The data determined by the sensor are in particular saved in a memory connected to the device at either defined or freely selectable intervals and, when required, either retrieved by telemetry or transmitted to a base station by telemetry.

The data from the base station, which can be either fixedly installed or take the form of a hand-held device, can be processed by a computer or another device appropriate for this task and, in a preferred configuration thereof, displayed.

A further embodiment of the invention provides that the body has a first region and a second region, wherein the first region of the body is radio wave transmissive and wherein the second region is configured to achieve an adequately high average density of the body.

Only thanks to the radio wave transmissibility of the first region is it possible to guarantee that the telemetric device can transmit the measurement data by radio from the stomach of the livestock animal. If a sufficiently high average density of the body is to be achieved, it is advantageous to manufacture the second region from a dimensionally stable, inert, biocompatible and sufficiently dense material, since most radio wave transmissive materials have a density which is too low to achieve an average density of the device which is adequately high to prevent excretion.

In one embodiment of the invention, the first region has an in particular cylindrical casing of a biocompatible polymer, wherein the telemetric device is arranged at least in places in the first region, and wherein the pressure sensor is arranged at an upper or free end of the first region, wherein in particular the hollow body adjoins the upper or free end of the first region and forms or at least in part bounds the gas-tight interior with the pressure sensor, or wherein in particular the upper or free end of the first region is closed by a gas-tight membrane which at least in part bounds the gas-tight interior.

This embodiment particularly advantageously combines the radio wave transmissibility of the first region with an economic and inexpensive material, namely a biocompatible polymer. Arranging the telemetric device in the first region ensures that transmission of the measurement data is guaranteed. Arranging the resilient material, either in the form of a projecting hollow body or alternatively in the form of a resilient membrane, at the end of the body or first region guarantees a comparatively simple structure of the body, which contributes to economically viable production.

Biocompatible means in this connection that the polymer does not release any poisonous or harmful substances in the livestock animal's stomach and does not trigger any contraindicative responses in the livestock animal.

The upper region of the first region is preferably shaped as the end piece of the body.

The second region advantageously has an in particular cylindrical casing which has a bottom on an underside of the first region, wherein the casing in particular includes stainless steel and wherein the casing comprises a receptacle for an energy source for the telemetric device, wherein the energy source may in particular be a primary or a rechargeable battery.

This embodiment can particularly advantageously be embodied in combination with the first region which includes a biocompatible polymer. The stainless steel in particular contributes to stability, compatibility (being inert) and to achieving the adequately high density of the body. Safe accommodation of the energy source can furthermore be guaranteed in this way.

The problem according to the invention is also solved, starting from the same concept of the invention, by a second device having the following features.

Such a second device for detecting the gastric motility of a livestock animal, in particular of a ruminant, has a first subbody and a second subbody, wherein the first subbody is connected to the second subbody via a joint, wherein the device has a position sensor which is designed to determine the position of the first subbody relative to the second subbody and wherein the first subbody in particular includes a device according to the above embodiments.

Such a joint may for example be a ball or alternatively also a hinge-like joint. In the broadest sense, any flexible connection, such as for example a short tape, between the first subbody and the second subbody is in particular suitable as the joint.

This second device determines gastric motility on the basis of the movements of the two subbodies and, like the above-disclosed device, embodies a means for detecting gastric motility.

In particular, a combination of the above-disclosed device with the second device solves the problem according to the invention with different and partially redundant means, which contributes to particularly reliable detection of gastric motility.

The problem according to the invention is furthermore solved by a method according to Claim 16 for measuring gastric pressure using a device according to the invention, wherein the method includes the following steps:

preferably orally introducing the device into the stomach of the livestock animal in such a manner that the device remains permanently, in particular until death or surgical removal, in the stomach of the livestock animal, measuring a time series of the pressure, transmitting the measurement data out from the stomach of the livestock animal.

The (in particular oral) introduction of the device into the stomach of the livestock animal need not necessarily constitute a step of the claimed method. The method can also start at a point in time at which said device has already been introduced or is present in the stomach of the livestock animal.

Alternatively, the invention can be claimed on the basis of the following feature-defining points in part or in whole, in particular together with features of the above-disclosed devices. It is here possible to combine the individual features of the points in isolated manner with the claimed features.

Point 1:

The invention relates to a device for detecting the motility of the stomach and/or alimentary tract of living organisms by means of one or more sensors and a telemetry device for transmitting the measured values to a receiver, characterized in that a gas- or fluid-filled, resilient hollow body located on the device in bolus form is deformed as a consequence of forces acting thereon and said deformation is recorded with a sensor. The deformation of the hollow body results from the movement of the organ in which said hollow body is located. If the deformation is the result of the movement of the stomach in which the device is located, the device permits measurement of gastric motility.

Point 2:

The device according to point 1, characterized in that the hollow body consists of a flexible material, preferably silicone, unvulcanised or vulcanised rubber or another suitable, chemically inert, resilient or flexible material.

Point 3:

The device according to point 2, characterized in that at least one sensor records the deformation of the flexible material. Said sensor may preferably be a pressure sensor or strain gauge.

Point 4:

The device according to point 3, characterized in that a microcontroller reads one or more sensors and temporarily stores the result or data in order to be able to retrieve it when required.

Point 5:

The device according to point 4, characterized in that a telemetry unit transmits the data to a receive unit, preferably a base station, automatically at a time interval which is defined or can be varied as required or alternatively or additionally on retrieval. The transmitted data from the device can be processed and, if required, displayed, at the receiver.

Point 6:

The device according to point 5, characterized in that the device is equipped with further sensors for measuring acceleration, temperature, conductivity or another physiological status parameter of the organism. These data can likewise be processed, stored and transmitted by telemetry for use on the receiver as explained in points 4 and 5 for the movement data.

Point 7:

The device according to point 6, characterized in that the device is operated with a fixedly connected energy source which permits operation of the device for approx. 60 days and beyond.

Point 8:

The device according to point 7, characterized in that the device is additionally equipped with at least one motion sensor with which the overall movement activity of the living organism is determined, and further additional sensors, such as temperature sensors or sensors for conductivity or pH.

Point 9:

The device according to point 8, characterized in that the device is in bolus form and the length of the bolus amounts to approx. 10-15 cm and its diameter to approx. 3-4 cm. The device has an overall density of preferably 2.3-3.0 g/cm$^3$, in particular 2.8 g/cm$^3$ or in particular of 2.3-2.5 g/cm$^3$, which guarantees that it comes to rest in the organ to be observed (for example the rumen in cattle) and is not unintentionally excreted.

Point 10:

The device according to point 9, characterized in that the carcass of the bolus consists of PVC (polyvinyl chloride), PEEK (polyetherether ketone) or POM (polyoxymethylene) and can be equipped with a ballast to achieve the desired mass.

Further features and advantages of the invention are explained below on the basis of the description of figures of exemplary embodiments in which.

Figure 1:
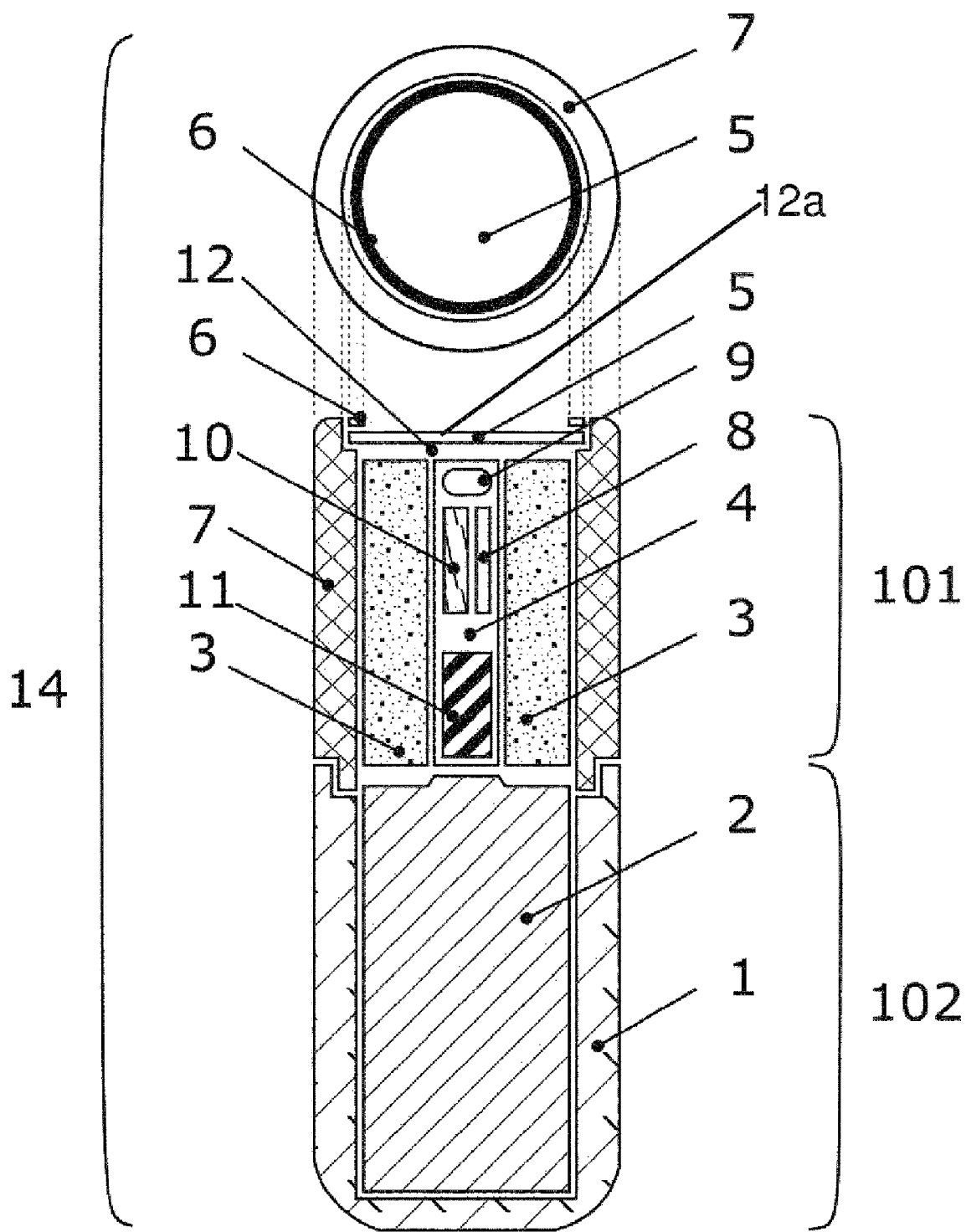
FIG. 1 shows two sectional views through a device according to the invention.

FIG. 1 shows two sectional views of a device according to the invention. The device has a body 14 in particular in bolus form, also optionally denoted bolus for short. The body 14 is subdivided into a first region or portion 101 and second region or portion 102. The first region 101 has a cylindrical casing 7 of POM. The casing 7 here comprises a packing piece 3, in which the electronics 4 of the body 14 are arranged. Selection of the polymer ensures on the one hand radio wave transmissibility and simultaneously on the other hand biocompatibility of the material.

The electronics 4 here comprise inter alia a telemetric device 8, a pressure sensor 9 and a microcontroller 10 and a memory device 11. The pressure-sensitive part of the pressure sensor is accommodated in a gas-tight interior 12 (or can communicate therewith), the wall 12a of which is at least in part likewise configured from the casing 7 of the first region 101 and the top of which (also part of the wall) is formed by a resilient membrane 5 of silicone rubber. The gas-tight interior 12 is here located at one end of the first region 101 of the body 14 and is preferably arranged on the end face of the elongate body 14.

Deformation of the membrane 5 as a result of application of force brings about a change in pressure in the gas-tight interior 12 which can be detected by the pressure sensor 9. The interior 12 is closed with a closure means in the form of a ring 6 which fixes the membrane 5 in place. The interior 12 is thus sealed in gas-tight manner. The electronics 4 are internally interconnected in such a way that the measurement data from the pressure sensor 9 can be processed by the microcontroller 10, stored on the memory device 11 and sent by the telemetric device 8 to an external base station. The measurement data can furthermore also be processed by the telemetric device 8 itself.

The second region 102 of the body 14 adjoins below the first region 101. The second region 102 has a cylindrical casing 1 (for example of a stainless steel) which comprises an energy source in the form of a battery 2 for supplying the electronics 4.

The electronics 4 are activated by means of a latching circuit which is triggered with a reed contact. To this end, a magnet closes the reed contact from outside and so activates the electronics 4.

The electronics 4 can turn back off as a result of an appropriate level on reset of the latching circuit, so enabling a test run of the entire body 14 or device.

Figure 2:
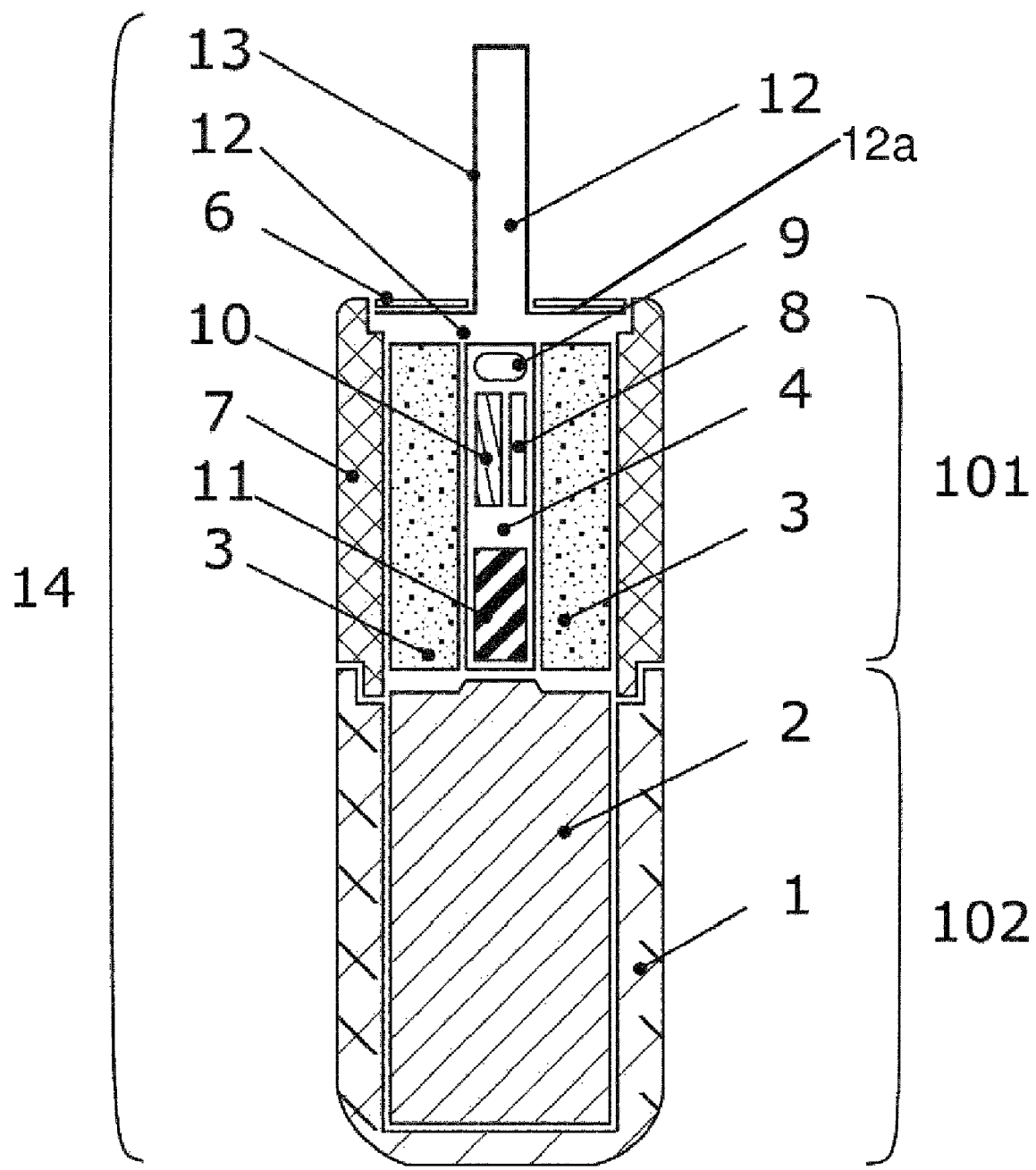
FIG. 2 shows a sectional view through a device according to the invention with a hollow body.

In contrast with FIG. 1, FIG. 2 shows a variant of the invention in which, instead of the resilient membrane 5, a resilient hollow body 13, for example of silicone rubber, projecting out from the body 14 forms or bounds the gas-tight interior 12 or a part of said interior 12. The hollow body 13 is here configured as a probe which can particularly advantageously detect the gastric motility of a livestock animal because it is preferably embodied such that it can be flexed. All the other components are arranged or configured in a similar manner to the features already shown in FIG. 1.

Figure 3:
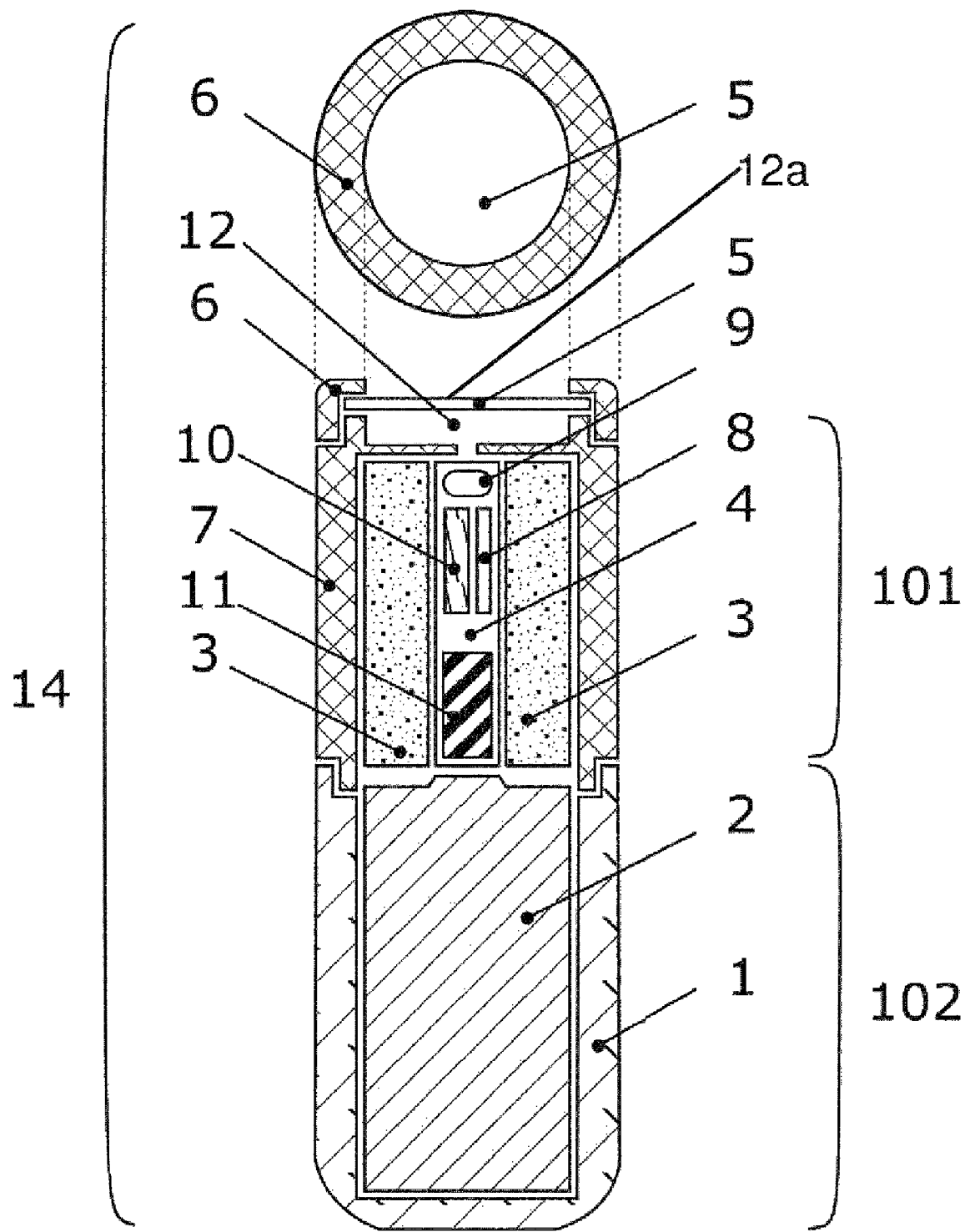
FIG. 3 shows a sectional view of a modification of the embodiment according to FIG. 1.

FIG. 3 shows a further configuration of the sensor system. The figure shows the casing 1, which protectively encloses the energy source 2, the packing piece or alternatively weighting body 3, the electronics 4, the flexible membrane 5, together with the sealing cap 6, the casing 7, the telemetric device 8, the pressure sensor 9, as well as the microcontroller 10 and the memory device 11, and the gas-tight interior 12.

In contrast with FIG. 1, the closure means 6 is here configured as an annular sealing cap 6 which is configured to be screwed together with the body 14, in particular the casing 7, wherein the membrane 5 is fixed in place over the interior 12. To this end, the closure means 6, when screwed together as intended with the body 14 or casing 7, presses the membrane 5 against a circumferential contact surface of the casing 7, wherein the membrane 5 is fixed to the body 14 or casing 7 and the interior 12 is sealed in gas-tight manner.

In particular, in an embodiment with a circumferential region, said annular sealing cap 6 presses against a circumferential edge region of the in particular circular membrane 5. The membrane 5 does not here project beyond the sealing cap 6 in the axial direction of the body 14, as a result of which the membrane 5 is provided with additional protection.

Further Development of the Invention

A further development of the invention is outlined below.

The period of operation of devices which require electrical current to function is limited for technical reasons (for example if the energy is supplied via a mobile energy storage device, for example a primary or a rechargeable battery). Long-term measurements in which the device, which may be a sensor or a sensor system, is accommodated in a living organism, such as for example a cow, naturally allow no ongoing physical access to the device.

Replacement of the energy supply in order to maintain the measurement task is then ruled out. In particular in "ruminal boli" [OE 600 17 916 T2] [WO 2011/079338 A2] [GB 2 455 700 A], in which the bolus is activated and then introduced orally into the rumen preferably of cows, it is no longer possible to exchange the bolus once it has been introduced in order to change the battery or sensor.

One unsatisfactory solution to this problem is to repeatedly administer a new bolus which has the disadvantage that this can only be done a limited number of times per living organism or individual animal. Replacement of an exhausted supply of active substance or an exchange in the event of malfunction has also not hitherto been possible. This problem is addressed by the further development of the invention.

In addition, reuse of the device by establishing a cycle in which the device is reprocessed would provide a sustainable and economically viable way of keeping costs low.

Increasing concerns regarding environmental protection would also be addressed by such planned handling of resources.

Object of the Further Development of the Invention

The field of application of the device is health monitoring or the administration of active substances to living organisms, preferably livestock. Since the device is exchangeable, the periods of operation are limited only by the possibility of exchanging the device.

Ruminal boli, as are for example used in cows for pH measurements in the rumen [OE 600 17 916 T2] [WO 2011/079338 A2] [GB 2 455 700 A], must have a minimum density of 2.3 g/cm³ for them to remain permanently in the reticulum (rumen). If the density is lower, such boli move onward in the digestive tract and ultimately leave it naturally and are excreted.

Accordingly, if such a sensor has the required minimum density on introduction or during operation and, in response to a specific signal, reduces its density or mass, a device is obtained which can remove itself as desired from the body via a natural pathway. Said device can then be replaced, ideally seamlessly, with a new one.

In a preferred embodiment, the change to the device can proceed by moving a piston which expels a solution present in the bolus. The consequence of this expulsion of a solution by piston movement would be a reduction in the total weight of the bolus. The device would experience additional buoyancy as a result of the change in volume or pressure of the piston chamber cleared by the piston.

In a further variant of the embodiment, the change to the device can proceed by jettisoning a ballast element.

Discharging a heavy fluid such as for example the non-toxic sodium polytungstate would also result in a reduction in mass. The device becomes correspondingly lighter as a result of each of the listed measures and can be excreted via the natural pathway since it no longer has the required density to remain in place.

A further variant embodiment consists in a gas being formed by initiating a chemical reaction or in gas passing from a pressure vessel into a flexible balloon or compartment, so reducing the density of the device.

The bolus, which is now lighter or has been changed in density, is excreted, whereas when a jettisoned ballast element is used, the latter remains in the reticulum. The aim of these measures is to modify the part of the device to be exchanged or the entire device in such a manner that it no longer meets the conditions for remaining in place in the organ to be investigated.

According to the invention, the device may be used for repeated use in living organisms or preferably in livestock husbandry. It may be equipped with sensors or sensor systems in order, in the digestive system of living organisms, to determine physiological parameters of an organ (for example pressure, temperature, pH, conductivity, movement activity).

These data may furthermore be retrieved or transmitted by telemetry. Furthermore, active substances may alternatively or additionally be delivered in targeted manner by means of a reservoir located in the device.

Exchangeability of the device opens up the possibility of permanent, sensor-controlled administration of an active substance or medication.

The shape of the device is primarily determined by its intended application. In the case of a ruminal bolus, it is accordingly of tube-like and rounded shape and has a conventional length of approx. 10-15 cm with a diameter of approx. 3-4 cm. When used as a ruminal bolus, the density on introduction into the rumen is preferably no less than 2.3-2.5 g/cm³ so that it will reliably remain therein.

The advantage achieved with the invention consists in the fact that, once a defined limit capacity of the energy supply is reached, the latter can straightforwardly be replaced without further intervention from outside. The energy consumption of the device is thus no longer the limiting factor.

It is likewise advantageous to be able to exchange or replenish a supply of an active substance.

A further significant advantage is that of being able to reprocess part of the device for reuse. According to the invention, this can involve recharging the excreted part of the device in order to put it to renewed use in a cycle.

The possibility of reuse also addresses environmental protection issues.

It is also advantageous that ageing effects or other defects of the sensors used, which are manifested for example in drift in the acquired measured values, are largely avoided.

This further development of the invention can be claimed in complementary manner with the claimed invention or also isolated with the following points, wherein also individual features of the further development of the invention can, insofar as is meaningful, likewise be claimed with the claimed invention.

Point 1w:

The invention relates to a device which is characterized in that, in response to a trigger, it undergoes a modification in its form and or a physical parameter, preferably its density or alternatively or additionally its weight, which is such that said device, when introduced into the gastrointestinal tract of a living organism, leaves the gastrointestinal tract again as a result of the change brought about by the trigger via a natural pathway, i.e. rectally or alternatively also orally.

Point 2w:

The device according to point 1w, characterized in that the mass, density and shape of the device in the initial state, i.e. for remaining in place in the target organ, are designed such that the device does not leave the target organ.

Point 3w:

The device according to point 2w, characterized in that, in response to a trigger, which according to the invention may for example be reaching a threshold voltage of the energy supply or alternatively or additionally another trigger, which results in the form and/or shape or density and optionally mass being modified such that according to the invention the position of the device in the organ in which the device is located is modified as a result of the modification in such a manner that the device leaves the alimentary tract via a natural pathway, either onwards rectally or conversely orally.

Point 4w:

The device according to point 3w, characterized in that the device is equipped with a mechanism which allows a ballast element to be detached from the device or, by movement of a piston, a solution to be expelled from the device or alternatively to fill a volume in the device with a gas or another light medium in order purposefully to modify the mass or density of the device.

Point 5w:
The device according to point 4w, characterized in that the device has a control unit which evaluates system parameters of the device or additionally parameters of sensors connected to the system as a trigger for the procedure stated in claim 4.

Point 6w:
The device according to point 5w, characterized in that the device is equipped with an energy supply which is rechargeable.

Point 7w:
The device according to point 6w, characterized in that the device is biologically compatible and safe for use in living organisms, preferably in livestock husbandry.

Point 8w:
The device according to point 7w, characterized in that the device is capable of delivering active substances from a reservoir in a targeted manner. Active substance delivery may proceed either permanently or in a targeted manner by an open- or closed-loop control circuit. According to the invention, exhaustion of the supply of active substance can be one of the triggers which brings about exchange of the device according to points 1w, 3w and 4w.

Point 9w:
The device according to point 8w, characterized in that the device has a telemetry unit with which it can exchange data with a measuring station.

The invention claimed is:

1. A device for detecting the gastric pressure of an animal, in particular of a ruminant, the device comprising:
a first subbody and a second subbody,
wherein the first subbody is connected to the second subbody via a joint, wherein the device has a position sensor which is designed to determine the relative position of the first subbody to the second subbody, wherein the first subbody in particular comprising:
a body (14) having the following components:
a pressure sensor (9),
a telemetric device (8) for transmitting measured values from the pressure sensor (9),
a gas-tight interior (12), one wall (12*a*) of the gas-tight interior (12) having a resilient region (5, 13) which is deformable by the gastric pressure of the animal, and the pressure sensor (9) being configured to detect the pressure in the gas-tight interior (12),
wherein the body (14) of the device is constructed in such a way that it permanently remains in the stomach of the animal When it has been administered to the animal, wherein the device comprises a motion sensor, wherein the motion sensor is designed to detect the movement activity of the animal.

2. The device according to claim 1, wherein the body (14) has an average density of greater than 2.3 g/cm$^3$ and in particular less than 3.5 g/cm$^3$, wherein the density is particularly preferably 2.8 g/cm$^3$.

3. The device according to claim 1, wherein the body (14) has a volume of between 50 cm$^3$ and 250 cm$^3$, preferably between 70 cm$^3$ and 160 cm$^3$, wherein the volume particularly preferably amounts to 150 cm$^3$.

4. The device according to claim 1, wherein the region (5) is configured as a resilient membrane (5).

5. The device according to claim 1, wherein said region of the wall (12*a*) of the gas-tight interior (12) is formed by a resilient hollow body (13) projecting out from the body (14), wherein the hollow body (13) is deformable by forces acting thereon in the stomach of the animal.

6. The device according to claim 4, wherein the membrane (5) or the hollow body (13) can be fixed to the body (14) by means of an annular sealing cap (6).

7. The device according to claim 5, wherein the hollow body (13) can be flexed by forces which arise from movements of the stomach of the animal and wherein the hollow body (13) is provided and configured to be flexed by said forces.

8. The device according to claim 5, wherein the hollow body (13) is of tubular, in particular cylindrical, configuration.

9. The device according to claim 1, wherein the device has a temperature sensor which is designed to detect a gastric temperature in the animal when the device is arranged in the stomach of the animal.

10. The device according to claim 1, wherein the telemetric device (8) is designed to process the measurement data of the pressure sensor (9) and in particular the measurement data of the temperature sensor and/or the motion sensor and to send the processed data to a receiver.

11. The device according to claim 1, wherein the body (14) has a microcontroller (10) and a data memory (11) in which the measurement data or the processed measurement data can be stored.

12. The device according to claim 1, wherein the body (14) has a first region (101) and a second region (102), wherein the first region (101) of the body (14) is radio wave transmissive and wherein the second region (102) is additionally constructed such that the body (14) has at least the average density.

13. The device according to claim 12, wherein the first region (101) has an in particular cylindrical casing (7) of a biocompatible polymer, wherein the telemetric device (8) is arranged in the first region (101) and wherein the pressure sensor (9) is arranged at an upper end of the first region (101), wherein in particular the hollow body (13) adjoins the upper end of the first region (101) and at least in part bounds the gas-tight interior (12), or wherein in particular the upper region (101) is closed at the upper end by the membrane (5) which at least in part bounds the gas-tight interior (12).

14. The device according to claim 12, wherein the second region (102) has an in particular cylindrical casing (1) which has a bottom on an underside of the first region (101), wherein the casing (1) in particular includes stainless steel and wherein the casing (1) comprises a receptacle for an energy source (2) for the telemetric device (9), wherein the energy source (2) may in particular be a primary or a rechargeable battery.

15. A method for measuring gastric pressure using a device according to claim 1 having the steps of:
orally introducing the device into the stomach of the livestock animal in such a manner that the device remains permanently in the stomach of the livestock animal, measuring a time series of the pressure,
transmitting the measurement data out from the stomach of the livestock animal.

16. The device according to claim 1, wherein the motion sensor has an acceleration sensor.

17. The device according to claim 1, wherein the motion is sensor is completely integrated in the device.

* * * * *